United States Patent
Schaffert et al.

(10) Patent No.: US 10,062,174 B2
(45) Date of Patent: Aug. 28, 2018

(54) 2D/3D REGISTRATION

(71) Applicants: Roman Schaffert, Nürnberg (DE); Jian Wang, Forchheim (DE); Anja Borsdorf, Adelsdorf (DE)

(72) Inventors: Roman Schaffert, Nürnberg (DE); Jian Wang, Forchheim (DE); Anja Borsdorf, Adelsdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/436,808

(22) Filed: Feb. 18, 2017

(65) Prior Publication Data
US 2017/0243361 A1    Aug. 24, 2017

(30) Foreign Application Priority Data
Feb. 18, 2016 (DE) ........................ 10 2016 202 512

(51) Int. Cl.
*G06K 9/00* (2006.01)
*G06T 7/37* (2017.01)
(Continued)

(52) U.S. Cl.
CPC .............. *G06T 7/37* (2017.01); *A61B 6/5211* (2013.01); *A61B 6/5264* (2013.01);
(Continued)

(58) Field of Classification Search
None
See application file for complete search history.

(56) References Cited

U.S. PATENT DOCUMENTS

2015/0030229 A1   1/2015   Borsdorf et al.
2016/0335777 A1   11/2016  Borsdorf et al.

FOREIGN PATENT DOCUMENTS

DE    102013214479 A1    1/2015
DE    102015208929 B3    6/2016

OTHER PUBLICATIONS

Fischler, Martin A., et al. "Random sample consensus: a paradigm for model fitting with applications to image analysis and automated cartography." Communications of the ACM 24.6, pp. 381-395, 1981.

(Continued)

*Primary Examiner* — Atiba O Fitzpatrick
(74) *Attorney, Agent, or Firm* — Lempia Summerfield Katz LLC

(57) ABSTRACT

A method includes, following specification of an initial transformation as a test transformation that is to be optimized, determining a 2D gradient x-ray image and a 3D gradient dataset of the image dataset, carrying out, for each image element of the gradient comparison image, a check for selection as a contour point, and determining an environment best corresponding to a local environment of the contour point and extending around a comparison point in the gradient x-ray image for all contour points in the at least one gradient comparison image. Local 2D displacement information is determined by comparing the contour points with the associated comparison points, and motion parameters of a 3D motion model describing a movement of the target region between the acquisition of the image dataset and the x-ray image are determined from the displacement information and a registration transformation describing the registration.

30 Claims, 3 Drawing Sheets

(51) Int. Cl.
  G06T 7/32      (2017.01)
  G06T 7/246     (2017.01)
  G06T 7/269     (2017.01)
  G06T 7/207     (2017.01)
  G06T 7/564     (2017.01)
  G06T 7/38      (2017.01)
  G06T 7/00      (2017.01)
  G06T 19/00     (2011.01)
  G06T 11/00     (2006.01)
  A61B 6/00      (2006.01)

(52) U.S. Cl.
  CPC .......... *G06T 7/0016* (2013.01); *G06T 7/207* (2017.01); *G06T 7/248* (2017.01); *G06T 7/269* (2017.01); *G06T 7/32* (2017.01); *G06T 7/38* (2017.01); *G06T 7/564* (2017.01); *G06T 11/005* (2013.01); *G06T 11/006* (2013.01); *G06T 19/003* (2013.01); *G06T 2200/04* (2013.01); *G06T 2200/28* (2013.01); *G06T 2207/10028* (2013.01); *G06T 2207/10081* (2013.01); *G06T 2207/10088* (2013.01); *G06T 2207/10121* (2013.01); *G06T 2207/20016* (2013.01); *G06T 2207/20221* (2013.01); *G06T 2207/30008* (2013.01)

(56) References Cited

OTHER PUBLICATIONS

German Office Action for German Application No. 10 2016 202 512.0 dated Oct. 4, 2016, with English Translation.

Haber, Eldad, and Jan Modersitzki. "Intensity gradient based registration and fusion of multi-modal images." Medical Image Computing and Computer-Assisted Intervention—MICCAI 2006.

Hartley, Richard, et al. "Multiple view geometry in computer vision" Cambridge University Press, pp. 153-157, 161, and 162, 2003.

Kubias, Alexander, et al. "Extended global optimization strategy for rigid 2D/3D image registration." Computer Analysis of Images and Patterns, Springer Berlin/Heidelberg, pp. 759-767, 2007.

Liao, Rui, et al. "A review of recent advances in registration techniques applied to minimally invasive therapy." IEEE transactions on multimedia 15.5, pp. 983-1000, 2013.

Lucas, Bruce D., et al. "An iterative image registration technique with an application to stereo vision." pp. 674-679, 1981.

Scales J.A. et. al.: "Robust methods in inverse theory", in: Inverse Problems, vol. 4, pp. 1071-1091, 1988.

Tomazevic, et al. "Robust gradient-based 3-D/2-D registration of CT and MR to X-ray images." IEEE Transactions on Medical Imaging 27.12, pp. 1704-1714, 2008.

Wang, Jian, Anja Borsdorf, and Joachim Homegger. "Depth-Layer-Based Patient Motion Compensation for the Overlay of 3D Volumes onto X-Ray Sequences." Bildverarbeitung für die Medizin, pp. 128-133, 2013.

Wang, Jian, et al. "Depth-aware template tracking for robust patient motion compensation for interventional 2-d/3-d image fusion." 2013 IEEE Nuclear Science Symposium and Medical Imaging Conference (NSS/MIC), 2013.

Wang, Jian, et al. "Gradient-based differential approach for 3-D motion compensation in interventional 2-D/3-D image fusion." 3D Vision (3DV), 2014 2nd International Conference on. vol. 1. IEEE, pp. 293-300, 2014.

Wein, Wolfgang, et al. "2D/3D registration based on volume gradients." SPIE Medical Imaging, vol. 5747, pp. 144-150, 2005.

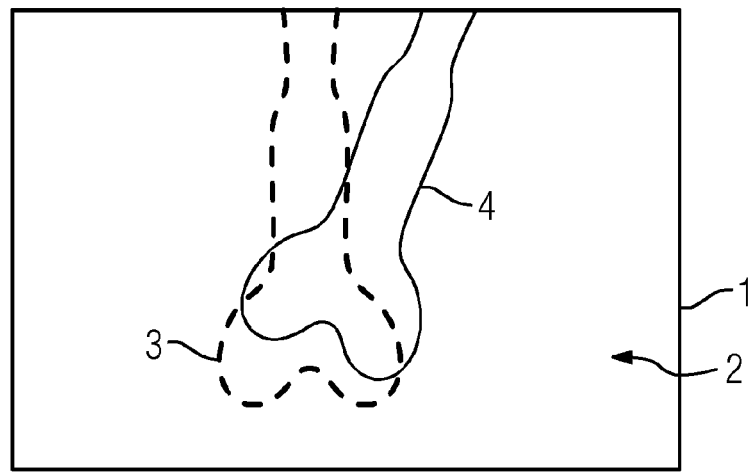
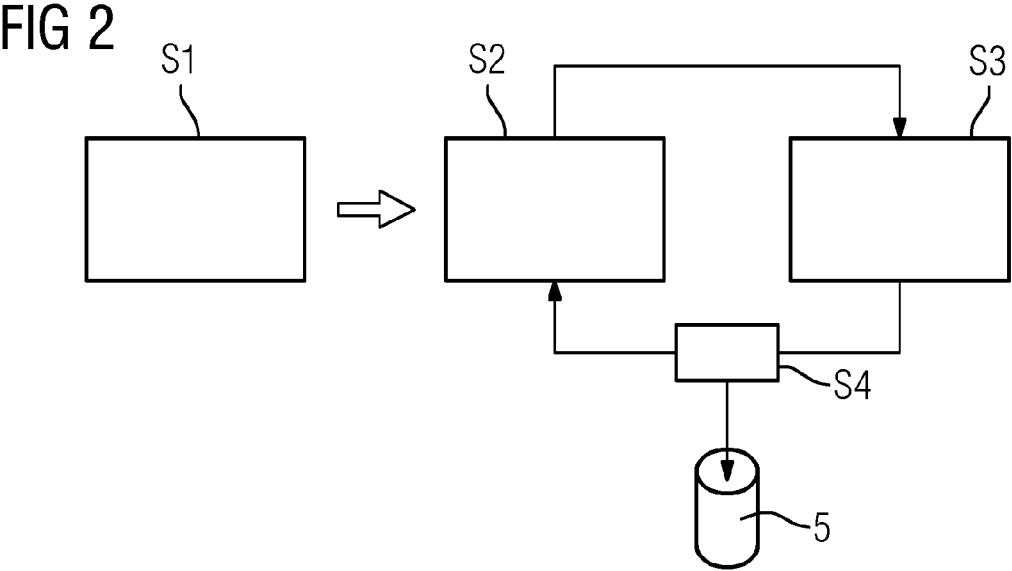

2D/3D REGISTRATION

This application claims the benefit of DE 10 2016 202 512.0, filed on Feb. 18, 2016, which is hereby incorporated by reference in its entirety.

BACKGROUND

The present embodiments relate to registering a three-dimensional image dataset of a target region of a patient with a two-dimensional x-ray image of the target region recorded in an acquisition geometry.

In many problematic medical situations, whether it be in diagnostics or when performing minimally invasive interventions, for example, both three-dimensional image data in the form of an image dataset (e.g., a computed tomography or magnetic resonance dataset) and two-dimensional fluoroscopic images (e.g., typically x-ray images) are available for the target region of interest of the patient. In such situations, it is desirable to be able to carry out a joint evaluation of both the three-dimensional image dataset and the two-dimensional x-ray image of the target region (e.g., in the form of a fusion image or by integrating features of one image into the respective other image). The coordinate systems of the three-dimensional image dataset and the two-dimensional x-ray image are to be correlated with one another. This process is usually referred to as registration (e.g., in the present case as 2D/3D registration).

The 2D/3D registration is particularly important in the context of image-guided medical interventions. In such cases, use is often made of x-ray devices having a C-arm on which an x-ray source and an x-ray detector are arranged opposite one another. The real-time monitoring of medical interventions by x-rays may be performed as fluoroscopy, which is why the x-ray images may also be referred to as fluoroscopic images. In the case of real-time guidance, preoperatively acquired three-dimensional image datasets (e.g., CT, magnetic resonance, etc.) may be superimposed as overlays onto the two-dimensional fluoroscopic x-ray images. The accuracy of the overlaying is important in terms of clinical applicability.

It is known in the prior art to perform a 2D/3D registration at the start of the intervention or the fluoroscopic monitoring in order to provide that the original accuracy is maintained. It may, however, happen during the medical intervention that the 2D/3D registration is rendered invalid due to movements of the patient (e.g., movements of the target region). In other words, misregistrations may occur. In order to eliminate this problem, it is known that the person carrying out the intervention may initiate a new registration procedure manually if the inaccurate overlay becomes clearly visible and thus is already able to affect the interventional procedure. In that event, the most recently acquired x-ray image is used to re-establish a 2D/3D registration. It is disadvantageous in this case that the person performing the intervention is interrupted during the interventional procedure as a result of the motion correction.

A different approach to keeping the 2D/3D registration updated provides that the patient, or at least the target region, is automatically tracked during the x-ray monitoring. A motion correction is thus enabled to be performed "on the fly." If the motion development is considered over time, it is also possible to predict the movement for future x-ray images. However, a valid, accurate 2D/3D registration at the outset is also to be provided for these tracking-based approaches in order to obtain correspondences for estimating the three-dimensional motion. However, the error occurring in the motion estimation is disadvantageously recognizable in the fusion or overlay images, since the tracking errors accumulate and 2D/3D correspondences are lost due to the movement.

Stated in general terms, various central factors of the 2D/3D registration may be identified. To be cited initially in this context as a first important factor is the similarity measure (e.g., comparison measure) used, which describes the accuracy of the 2D/3D registration. Typically, the image intensities (e.g., grayscale value) and gradients are used. The method utilized in the main for 2D/3D registration according to the prior art is the determination of a digitally reconstructed radiograph (DRR). This is a simulated x-ray image for the three-dimensional image dataset, which is therefore determined by forward projection (cf., for example, the article by A. Kubias et al. titled "Extended global optimization strategy for rigid 2D/3D image registration," in: CAIP, LINCS, Volume 4673, Springer (2007), pp. 759-767). Comparison measures based on the intensity values of the DRR image and the x-ray image may be used as a similarity measure (e.g., the sum of absolute differences (SAD), the sum of squared differences (SSD), and the normalized cross-correlation (NCC)). Examples of gradient-based comparison measures are the gradient cross-correlation (cf. W. Wein et al. titled "2D/3D registration based on volume gradients," in: Medical Imaging SPIE (2005), pp. 144-150), and the normalized gradient field (NGF) (cf. E. Haber and J. Modersitzki, "Intensity gradient based registration and fusion of multi-modal images," MICCAI 2006). These measures are usually regarded as a more robust alternative to intensity-based comparison measures.

Also relevant, for example, with regard to movements occurring in the target region, is the applied motion model. The image registration is generally known as an optimization method in which motion is applied to the moving image in order to bring the moving image into correspondence with the stationary image. In this case, the motion may be applied for rigid structures as a rigid movement and articulated (e.g., partially rigid) movement, but also as an elastic movement in which, as a consequence, deformations may also occur. From the viewpoint of the dimensionality, either three-dimensional motion is applied to the three-dimensional image dataset or two-dimensional motion is applied to the two-dimensional x-ray image (e.g., projected two-dimensional x-ray image; DDR). For examples, in this regard, reference is made to the review article by R. Liao et al. titled "A review of recent advances in registration techniques applied to minimally invasive therapy", in: IEEE Transactions on Multimedia, 15 (5), 2013, pp. 983-1000.

The optimization strategy may be cited as a third important factor. Based on the selected comparison measure (e.g., similarity measure) and the motion model, a numerical optimization method that uses motion parameters of the motion model as parameters to be optimized is performed in order to maximize the similarity or in order to minimize the difference. In this case, gradient-based optimization methods may be applied with respect to the comparison measure. However, gradient-free optimization methods may also be employed. In the already cited article "Extended global optimization strategy for rigid 2D/3D image registration," for example, A. Kubias et al. propose using an extended global optimization strategy, where an adaptive random search is used at different coarse resolution levels and a local optimizer is applied to a higher resolution level in order to refine the registration. In the tracking-based approaches, the optimization is often based on mathematical relationships between tracked features and the three-dimensional rigid motion model.

In spite of all of the known approaches, the 2D/3D registration, which, for example, is intended to be performed in real time, still continues to represent a challenge. A category of known methods attempts to enable the three-dimensional motion by comparing the projection of the three-dimensional image dataset with the two-dimensional x-ray image (cf., the already cited publications by A. Kubias et al., W. Wein et al., and E. Haber et al.). However, the optimization is rendered more difficult in this case by the loss of the depth information, which occurs as a result of the projection. Another category of known methods uses the back-projection of the x-ray image and compares this with the three-dimensional image dataset, though these approaches require a plurality of two-dimensional x-ray images acquired from different projection directions (e.g., using different acquisition geometries), which is often not the case in medical interventions.

The tracking-based approaches have the advantage that the three-dimensional motion is determined by two-dimensional tracking. However, the tracking-based approaches require a high-quality initialization as well as a reinitialization in order to establish original 2D/3D correspondences or to reestablish the correspondences. DE 10 2013 214 479 A1 proposes a method for tracking a 2D/3D registration during movement in which contours are tracked in sequentially acquired projection images. A target plane may be determined for a given contour point in the two-dimensional x-ray image and an associated starting point in the three-dimensional image dataset. The target plane, the contour point displaced due to the movement, the starting point displaced due to the movement, and the focus (e.g., ultimately, the radiation source in the acquisition geometry) are located in the target plane. A relationship that connects the observable degrees of freedom of movement perpendicular to the course of the contour in the three-dimensional image dataset with general three-dimensional descriptions of the movement (e.g., motion parameters of a motion model) may be established. This equation system may be underdetermined in the case of a single contour point. However, since a plurality of contour points are considered here, an equation system that may be solved in order to determine the motion parameters and consequently to update the motion information results. This process exploits the fact that the contour may be associated with a rigid object that may consequently be mapped by common motion parameters describing a rigid movement. However, the problems of accumulating tracking errors also occur in this case, as does the potential loss of 2D/3D correspondences. With regard to this approach, reference is made to the article by J. Wang et al., titled "Gradient-Based Differential Approach for 3-D Motion Compensation in Interventional 2-D/3-D Image Fusion," Proceedings of the 2014 International Conference on 3D Vision, pp. 293-300.

In order to improve this concept, and to permit a robust and accurate registration also starting from less exact 2D/3D correspondences and/or, for example, over a longer series of acquired x-ray images, it is proposed in DE 10 2015 208 929 A1 that after an initial transformation has been specified as a test transformation that is to be optimized, at least one rigid reference structure visible in the x-ray image is selected with an associated contour from anatomical structures contained in the image dataset determined in an evaluation. A two-dimensional gradient x-ray image and a three-dimensional gradient dataset of the image dataset are determined. After this, at least one two-dimensional gradient comparison image forward-projected in the acquisition geometry using the test transformation is determined from the gradient dataset of the x-ray image. An environment that best corresponds to a local environment of the contour point based on a comparison measure and extends around a comparison point in the gradient x-ray image is found for a plurality of contour points on the three-dimensional contour of the at least one selected reference structure in the acquisition geometry of the x-ray image in the gradient comparison image from environments extending around test points in the gradient x-ray image. Local two-dimensional displacement information is determined by comparing the contour points with the associated comparison points. Motion parameters of a three-dimensional motion model that describe a movement of the target region between the acquisition of the image dataset and the x-ray image are determined from the local two-dimensional displacement information and a registration transformation describing the registration by correcting the test transformation based on the motion parameters.

In the method disclosed therein, the registration process is therefore based on specific reference structures (e.g., hence on a sparse mapping), instead of using the entire image. The spatial image gradient is used in the comparison instead of the image intensity, since strong gradients contain the most structural information. The search for comparison points corresponding to starting points is conducted locally in a two-dimensional manner between the gradient x-ray image and the gradient comparison image, since the actually observable movement was merely projected and consequently may be different locally within the projection. Ultimately, however, with use being made of the rigid properties of the reference structures, a motion model that contains both the observable and the non-observable movement is used.

The method disclosed therein therefore includes the following steps. First, an initialization, in which, for example, an only roughly required initial registration is specified as an initial transformation, takes place. Next, reference structures are selected (e.g., contours in the three-dimensional image dataset that are to be tracked). Comparison points associated with the contour points are found in the two-dimensional x-ray image by a gradient-correlated matching. After this, the motion estimation may be performed (e.g., based on a point-to-plane correspondence), as was proposed in DE 10 2013 214 479 A1 and may be refined further in accordance with DE 10 2015 208 929 A1.

An aspect common to the approaches described in DE 10 2013 214 479 A1 and DE 10 2015 208 929 A1 is that usually a dense set of contour points or starting points is used in order to represent the surface/contour of the structure of interest. This is not computationally efficient for a real-time application such as is desired to be realized. Moreover, a volume analysis (e.g., 3D Canny) is necessary to determine the three-dimensional contour points or starting points. For this purpose, large amounts of both computational resources and memory resources are to be provided.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a more efficient and more sparse determination of suitable contour points is provided.

In one embodiment, a method for registering a three-dimensional image dataset of a target region of a patient with a two-dimensional x-ray image of the target region recorded in an acquisition geometry is provided. After an initial transformation has been specified as a test transformation that is to be optimized, a two-dimensional gradient x-ray image and a three-dimensional gradient dataset of the image dataset are determined. After this, at least one two-dimensional gradient comparison image forward-projected in the acquisition geometry of the x-ray image using the test transformation is determined from the gradient dataset. Depth information describing the depth in the radiation direction of the central beam of the acquisition geometry is associated in the gradient comparison image with the gradients described two-dimensionally in the image plane. A check is carried out for each image element of the gradient comparison image to determine whether the gradient described two-dimensionally in the image plane satisfies a selection criterion indicating the presence of a contour in the image element. All image elements satisfying the selection criterion are selected as contour points. An environment that best corresponds to a local environment of the contour point based on a comparison measure and that extends around a comparison point in the gradient x-ray image is found for all contour points in the at least one gradient comparison image from a plurality of environments extending around test points. Local two-dimensional displacement information is determined by comparing the contour points with the associated comparison points. Motion parameters of a three-dimensional motion model that describe a movement of the target region between the acquisition of the image dataset and the x-ray image are determined from the local two-dimensional displacement information and a registration transformation describing the registration is determined by correcting the test transformation on the basis of the motion parameters.

According to one or more of the present embodiments, a development of the method proposed by DE 10 2015 208 929 A1 is therefore disclosed. In the dynamic registration approach described therein, the selection of the starting points (and consequently contour points) was namely non-trivial for a variety of reasons (e.g., because the projected contour points typically cover the regions of two-dimensional interest in a redundant manner, with the result that unnecessary computational operations are required, and because a selection of the projected contour points performed anyway does not ensure a useful distribution of the contour points, with the result that a prejudiced motion estimation may occur due to loss of information). An improved dynamic registration process, in which the selection of starting points in the three-dimensional image dataset is avoided and instead contour points are selected directly in the two-dimensional gradient comparison image, is therefore provided. Since at least one piece of depth information is provided in the gradient comparison image, as will be explained in more detail hereinbelow, it is possible, after the selection of a contour point, to estimate the associated three-dimensional starting point in the three-dimensional image dataset at least with sufficient accuracy in order to perform the necessary calculations. For example, a problem formulation for calculating the motion parameters that henceforth requires the starting point only implicitly may be provided.

Therefore, a depth-aware gradient projection for the purpose of determining the gradient comparison image is performed initially in order to determine contour points. Those image elements that have prominent (e.g., therefore, particularly strong) gradients are selected as contour points, since such strong gradients point to edges in the image. The at least estimated three-dimensional positions may be determined using the corresponding depth information.

It is thus then possible to proceed further as known from DE 10 2015 208 929 A1, as will be explained in more detail hereinbelow.

Since operations are image-based and performed in the 2D domain, the approach according to one or more of the present embodiments is particularly suitable for realizing a multiple resolution scheme in which progress is made successively toward lower resolutions. Overall, the method according to one or more of the present embodiments offers a more efficient possibility for finding contour points (and the associated three-dimensional starting points in the three-dimensional image dataset), which may be utilized, for example, in connection with the known point-to-plane correspondence model described by the cited publications. The proposed operation on the gradient comparison images avoids a complex and time-consuming volume analysis. If, as already mentioned, a multiple resolution scheme is used or if the process is essentially initiated based on a coarser resolution, the selected contour points are sparsely distributed; overlaid contour points and redundant calculations are avoided. Accordingly, computational efficiency is fundamentally increased, and consequently, the real-time capability of the registration is significantly improved.

One embodiment provides that a plurality of gradient comparison images are determined for different depth intervals of the image dataset in the radiation direction of the central beam of the acquisition geometry The respective depth interval is assigned as depth information to the gradient comparison image. It is therefore provided that the target region covered by the three-dimensional image dataset is subdivided along the direction of the central beam of the acquisition geometry into subregions described by depth intervals, with separate gradient comparison images being determined for each of said subregions and hence, for each depth interval. This has the advantage that an overlapping of structures from different depths that are visible in the image dataset is avoided. A classification of the type into depth intervals is already known in principle in the prior art and has been described, for example, in the article by J. Wang et al. titled "Depth-Layer-Based Patient Motion Compensation for the Overlay of 3D Volumes onto X-Ray Sequences," in: BVM (2013), pp. 128 to 133. A variant of a depth-aware gradient projection (DGP) is realized as a result. In DGP, the rendering of the gradient comparison images takes place separately for different depth intervals, so that, for example, in the consideration of bone structures lying at different depth intervals, no undesirable calculation problems may occur due to the overlaying thereof. For example, effects in the overlaying in comparison with the gradient x-ray image, which is not depth-resolved, are intercepted by corresponding threshold values for comparison measures.

In one embodiment, a different subdivision of the target region (e.g., into subregions associated with reference structures that are suitably clearly mapped in x-ray images, though as a result, it would then be necessary to perform more complex calculations, which are precisely what are to be avoided in the present case) may be provided. A partitioning into depth intervals is simple to implement and already adequate in the majority of cases.

If depth intervals of the type are used, the depth interval assigned to a gradient x-ray image already indicates at least roughly the depth at which a starting point of the three-dimensional image dataset associated with a contour point is located. For example, it may be assumed here that the latter lies in the center of the depth interval, which may not be chosen as particularly large.

For each gradient comparison image, the depth position in relation to the radiation direction of the central beam in the acquisition geometry in the depth interval covered by the gradient comparison image, at which a maximum contribution to the gradient occurred during the forward projection, may be assigned as depth information to each gradient described two-dimensionally in the image plane (e.g., independently of the depth intervals). Should no DGP with a partitioning of the target region into subregions be performed, the depth interval corresponds to the entire area covered by the target region. Since the greatest contribution to the gradient projected into the image plane by forward projection may correspond to the edge that is responsible for producing the visible contour in the two-dimensional image plane, the third dimension may therefore be encoded in a superlative manner. The third dimension may be used in order to locate with maximum accuracy a three-dimensional starting point in the three-dimensional image dataset. The three-dimensional starting point is projected as a contour point into the image plane. Specifically, with regard to the partitioning of the target region into subregions having different depth intervals, this presents itself as suitable for the more accurate determination of starting points associated with contour points determined based on the selection criterion.

One embodiment provides that the gradient comparison image is determined by applying a render algorithm to the gradient dataset. In this case, one result channel of the render algorithm contains a normalized angular value as a direction indication of the gradient in the image plane and a further result channel contains a measure for the magnitude of the gradient in the image plane. In the present method also, therefore, the gradient in the image plane is not determined from digitally reconstructed radiograph (DRR) images forward-projected from the three-dimensional image dataset, but is rendered directly. This prevents a "false" gradient in the image plane by direct manipulation of the three-dimensional gradient of the gradient dataset, whereas "false" gradients may occur if two-dimensional image gradients are determined from DRR images. An example of this is the occurrence of false edges, which are produced due to artificially resulting limitations during the partitioning into depth intervals. A further advantage of direct volume rendering from the gradient dataset is that the render operation may be carried out in a single step on a graphical processing unit (GPU). In one embodiment, the render algorithm is executed by a GPU. An extremely fast and efficient calculation is possible by this, since hardware that is specifically configured for performing such render operations is used.

The gradient projection rendering is in this case configured specifically to fit the dynamic registration framework, with the rendering being performed separately for each subregion when the target region is partitioned into subregions. Conventional render algorithms or programming languages for adapting render algorithms of the type (e.g., GLSL) expect data within a normalized interval [0,1] in the result channels (e.g., up to four). A result channel may thus be used in order to specify the normalized angle of the gradient direction in the image plane (e.g., by division of the actual angle by $2\pi$). A further result channel is used in order to map the gradient magnitude or gradient absolute value, where, for example, $$g_{\|-1\|} = \frac{1}{1 + \|g\|}$$

may be used.

A third result channel containing the depth position normalized by the extension of the covered depth interval may beneficially be used in the determination of a depth position as depth information, as described hereinabove. A third result channel may therefore contain the depth position, normalized by the maximum depth, of the sampling position with the maximum gradient contribution. In this way, a depth-aware gradient projection (DGP) is generated that, in a single render step, also produces the depth estimation in addition to the gradient projection.

The selection criterion may include a threshold value comparison for the magnitude of the gradient described two-dimensionally in the image plane. In this case, it is assumed at the outset that when the magnitude of the gradient described two-dimensionally in the image plane (e.g., of the gradient of the gradient comparison image) exceeds a threshold value, a visible edge is given in the associated image element. More complex considerations may also be applied. For example, subcriteria of the selection criterion that take into account an environment of the image element that is currently under consideration may be formulated.

In one embodiment of the method, the gradient x-ray image and the gradient comparison image are initially determined in a coarser resolution with larger image elements than the x-ray image. The determination of the motion parameters and the correction of the test transformation are repeated successively in order at least to provide a better resolution (e.g., up to the resolution of the x-ray image). As has already been indicated, the image-based analysis conducted in order to find contour points is particularly suited to such a multiple resolution scheme, by which consideration is initially given to larger image elements that combine smaller image elements of the size of the image elements of the x-ray image. This has several advantages. In this way, the size of the area in which movements relative to the three-dimensional image dataset are captured may be increased, since the algorithm initially reacts less sensitively. The robustness of the procedure is therefore increased significantly. A type of "pyramid representation" is therefore given, where, for example, resolutions may be increased from 64×64 image elements, through 128×128 and 256×256 image elements, to 512×512 image elements. In this way, the accuracy of the determination of the motion parameters, and consequently the registration transformation, is improved incrementally.

If a plurality of image elements of the size of the image elements of the x-ray image are to be combined, a way is to be found with respect to the gradients to specify a useful gradient for the larger image element. The gradients (e.g., the direction thereof) of a larger image element formed by a plurality of image elements of the size of the image elements of the x-ray image may be determined at least for the gradient x-ray image from the structure tensor of the larger image element. If, therefore, a type of "field" (e.g., patch) composed of smaller image elements (e.g., a 4×4 patch) is considered as a larger image element, the center of the larger image element may, for example, be considered as a point position. Various possibilities exist for the gradients for the purpose of specifying a gradient value and a gradient direction for a "patch" of the type, which may be defined, for example, by a grid overlaid onto the 2D image. In other words, a method is to be selected in order to specify the gradient direction and the gradient value of an image element at a coarser resolution. Instead of selecting the gradient value in the center of the larger image element, the structure tensor at the center point within the window that defines the larger image element may be used. This is of advantage, for example, when the Kanade-Lucas-Tomasi tracker (KLT tracker) is used (cf., B. Lucas "An Iterative Image Registration Technique with an Application to Stereo Vision," IJCAI 81 (1981), 647-679), since the structure tensor provides a better numeric condition. In the approach described here, the eigenvectors and the eigenvalues of the structure tensor are used in order to define the gradient direction of a larger image element as a "patch" of smaller image elements. An alternative embodiment is the immediate calculation of a central gradient within the larger image element.

One embodiment provides the method be repeated iteratively with the registration transformation as a new test transformation until an abort criterion (e.g., the undershooting of a threshold value for a norm of the motion parameters and/or the undershooting of a specific number of iteration steps) is satisfied. If, therefore, a registration transformation has been found as a result of correcting the test transformation, an abort criterion may be checked. If the criterion is not satisfied, the registration transformation (e.g., instead of the initial transformation) is applied as the test transformation, and the corresponding acts may be repeated. In this case, the same starting points (e.g., reference structures) may be retained (e.g., while it is checked whether the contour points of gradients corresponding to the new test transformation in the gradient comparison image also satisfy the selection criterion), and computational objects such as gradient images/gradient datasets that have only been determined once and are independent of the test transformation may also be retained. The iteration therefore relates mainly to a repetition of the 2D/3D tracking until convergence is reached.

The method according to one or more of the present embodiments reduces the computational overhead by mapping the reference structures as a sparse representation and enabling operation to be performed on a two-dimensional basis. With the iterative approach, work is focused, for example, on the starting points and the contour points associated therewith. The comparison method is henceforth performed locally. Once a 2D/3D correspondence has been found locally, the 2D/3D correspondence may not be lost in further iterations. In the proposed approach, a gradient comparison image is generated directly from the three-dimensional image dataset. The search area for the 2D/3D tracking may be based on the image contents (e.g., as explained in more detail below, on the gradient direction). In this way, the method provides valid registrations both at the start of a medical intervention and during the further course thereof, as well as in pauses during the acquisition of the x-ray images. Since the three-dimensional image dataset is generally taken as the basis, there is also no further accumulation of tracking errors, because an accurate registration between the three-dimensional image dataset and the two-dimensional x-ray image is established immediately. In a certain manner, the method therefore provides a natural initialization (e.g., reinitialization) for the differential motion compensation (e.g., when the initial transformation is based on the registration transformation established in the previous time increment). In this way, the motion compensation framework becomes more reliable, since no errors accumulate and a refinement of the registration ultimately occurs automatically when it becomes necessary. Persons performing a medical intervention are able to concentrate more on the intervention procedure without being interrupted by misregistrations and the like.

As has already been mentioned, an extremely coarse approach for the initial transformation is already sufficient within the scope of the initialization in order to obtain reliable, valid 2D/3D registration results. For example, it may be provided that the initial transformation (e.g., the transformation used first) is a coarse transformation having an accuracy of, for example, <20 mm or <10 mm with respect to translation, and/or <10° or <5° with respect to rotations. In image acquisitions based on phantoms subject to preconditions of +/−5° for the rotation and +/−11 mm for the translation, a 100% success rate has been achieved (e.g., based on a success criterion requiring a 3D registration error of less than 2 mm). Outstanding success rates of up to 96.5% for head phantoms have been achieved even in the case of greater deviations. Excellent, accurate 2D/3D registrations are typically achieved after 5 to 10 iterations.

A suitable initial transformation may already be determined with sufficient accuracy from a known position of the patient relative to the x-ray device acquiring the x-ray image. When positioning patients inside an x-ray device having, for example, a C-arm (e.g., for a medical intervention), the position of the patient, and therefore the location of the target region, is in most cases already known very precisely, while the acquisition geometry and the geometric properties of the x-ray device are also available. Thus, given a known acquisition geometry, the initial transformation may be estimated with sufficient accuracy so as to lead to sufficiently reliable success in the 2D/3D registration (e.g., given suitable parameterization of the registration algorithm provided (e.g., insofar as the extent of the environments and/or the search area are concerned).

Other registration methods may also be used for determining the first initial transformation such that, for example, a coarse transformation determined from a registration process using forward-projected virtual x-ray images (DRR) and performed, for example, at a coarser resolution may be used as an initial transformation. This may be provided, for example, prior to the start of a medical intervention if there is still time available.

As has already been mentioned, the present method is suitable, for example, for the fluoroscopic x-ray monitoring of, for example, minimally invasive medical interventions. In this context, it is beneficial if a time series of x-ray images is acquired (e.g., for the purpose of monitoring a medical intervention). A registration is performed for each x-ray image, and the registration transformation determined for the x-ray image acquired immediately beforehand is used in each case as the initial transformation. Since there is typically only a short time interval between the acquisitions of x-ray images succeeding one another in time, particularly strong movements are unlikely to occur in the target region, so that the final registration transformation in relation to the previously acquired x-ray image is suitable as an initial transformation for the next registration process. A quality of the initial transformation known in this way may also be used, as already mentioned, in order to adapt parameters, for example, with regard to the described 2D/3D tracking, such that an embodiment provides that in the case of a registration transformation determined for an x-ray image acquired immediately beforehand as the initial transformation, a smaller environment and/or a smaller number of test points are/is chosen than in the case of some other initial transformation. If, for example, the x-ray image has a resolution of 512*512 pixels, an environment equal in size to 20*20 pixels or image elements may be applied in the case of a large assumed deviation of the initial transformation (e.g., at the time of the first determination of a registration transformation from a coarse transformation; initially, while the environment used for the comparison may be reduced to 5*5 pixels or image elements when registration transformations of preceding x-ray images are used). Similarly, a smaller number of test points or a smaller search area may be chosen.

As has already been explained, the visible misregistration due to transformation of the actual images may be regarded as the most intuitive way to perform an image registration. In the 2D/3D registration provided, the non-correspondence (e.g., the displacement) with respect to the reference structures is mainly identified by regions of clearly recognizable image gradients. For this reason, a gradient comparison image derived from the gradient dataset is obtained by gradient projection.

The gradient projection theorem is used with particular advantage in order to determine the gradient comparison image. The gradient projection theorem was proposed in an article by H. Livyatan et al. titled "Gradient-based 2D/3D rigid registration of fluoroscopic X-ray to CT," IEEE Transactions on Medical Imaging 22 (11) 2003, pp. 1395-1406. In this case the projected gradient comparison image, designated here by $\nabla I^{proj}$, at a point p in the image plane is yielded as $$\nabla I^{proj}(p) \propto \begin{pmatrix} h^T \\ v^T \end{pmatrix} \cdot r(p) \int_\lambda \lambda \cdot \nabla V(p(\lambda)) d\lambda, \qquad (1)$$

where h and v denote the horizontal and the vertical direction of the image plane, respectively, r(p) is the Euclidean distance between the pixel position p and the camera center C, and $p(\lambda)$ is a point on the beam that is back-projected from p and is given by the linear equation $p(\lambda)=\lambda p+(1-\lambda)c$.

In the following, stated in general terms, a comparison measure is now formed between a plurality of environments (e.g., test environments) of the gradient x-ray image and an environment of the contour point in the gradient comparison image. The comparison is local, which provides the size of the test environments and of the environment of the contour point does not correspond to the size of the overall gradient comparison image, but is typically significantly smaller, as is apparent from the already cited examples (e.g., in the range of 5*5 pixels to 20*20 pixels in the case of a 512*512 image). The environment of the contour point in the gradient comparison image is therefore called upon and compared with test environments that are associated with different test points in the gradient x-ray image by determining the comparison measure. In this case, there are a plurality of test points available that typically include a base test point corresponding to the contour point. Further test points are neighbors to the base test point (e.g., in the direction of the three-dimensional gradient), projected onto the image plane, as may be inferred from the gradient dataset based on an estimation of the starting point associated with the contour point or in an estimated manner from the gradient comparison image at the contour point. The latter approach is useful, for example, when working with a plurality of depth intervals across the target region, since influences from other depth layers (e.g., subregions) are eliminated to a large extent and the projection in the gradient comparison image associated with the depth interval substantially corresponds to that of the three-dimensional gradient at the starting point. A projected gradient may also be determined for larger image elements in the case of a multiple resolution approach, as described, for example, based on the structure tensor.

One embodiment accordingly provides that test points along the direction of the gradient projected onto the image plane are chosen in the starting point associated with the contour point in addition to a base test point corresponding to the contour point. When working with a plurality of depth intervals, the direction of the gradient at the contour point in the gradient comparison image may be resorted to directly for this purpose. The three-dimensional gradients are therefore taken into account at least implicitly when the search direction for finding correspondences is specified. In this case, this is an intuitive search direction, since the projection of the three-dimensional gradient ultimately indicates precisely the direction in which movements may be observed. Accordingly, a targeted search that operates with significantly reduced resources and contributes to the real-time capability of the described approach may be performed. The search direction is chosen based on the image contents, instead of, as in conventional practice, in an optimization method based on gradients of the parameters that are to be optimized.

Various concrete approaches may be provided in this case. Thus, comparison measures may be determined for a specific number of test points corresponding in each case, for example, to an image element, and the test point associated with the comparison measure indicating the greatest correspondence may be chosen as the comparison point. In this case, therefore, a specific search space (e.g., in the search direction at least implicitly defined by the three-dimensional gradient) is specified, starting, for example, from the base test point (e.g., in each case, five neighbor pixels lying in the starting point in the direction of the three-dimensional gradient projected onto the image plane). Alternatively, the test points may be chosen by an optimization algorithm maximizing the comparison measure and operating, for example, along the direction of the projected three-dimensional gradient in the starting point associated with the contour point. In this case, as is already known in principle, a search for a maximum correlation is conducted in increments, although the search direction may continue to be specified as described.

In this context, the test points and/or the number of test points to be used may be determined as a function of deviation information describing, for example, as an estimated value, the degree of the present deviation of the test transformation from reality. Thus, if it is known that the test transformation already represents a very good estimation, a search area may be reduced in order to obtain the best correlation, since it is only necessary to search through the immediate neighborhood of the base test point. For example, motion parameters of at least one registration process in relation to an x-ray image acquired at an earlier time and/or prediction information derived therefrom may be used as deviation information, as has already been explained with respect to the size of the environment. In one embodiment, the associated displacement information is discarded if a minimum value for the comparison measure at the comparison point is undershot. This provides that a specific minimum correlation is presumed in order even to be allowed to assume that the correct comparison point corresponding to the three-dimensional contour (e.g., the three-dimensional starting point) has been found. Such an approach is beneficial, for example, when, as has already been explained, work is focused on subregions of the three-dimensional image dataset that are examined separately, since in that case it is possible, for example, to remove from further consideration contour sections in the gradient comparison image that are affected by effects of the overlaying of an object from a different subregion.

Using the gradient correlation as a comparison measure has been proven to be particularly beneficial. The variable was introduced already as a comparison measure in the above-cited article by W. Wein et al. and may also be particularly advantageously applied within the scope of the present embodiments.

An exemplary embodiment for finding the best correspondence of the projected contour points in the gradient x-ray image may therefore provide, for example, that an environment $\Omega_N(\nabla I^{proj}, p_j)$ is defined for each contour point. The environment represents the neighborhood of the contour point $p_j$ in the gradient comparison image. In this case, N describes the size of the environment. Correspondingly, $\Omega_N(\nabla I^{fluoro}, p'_j)$ represents the environment of a test point $p'_j$ in the gradient x-ray image, where $p'_j$ lies on the search direction defined by the three-dimensional gradient in the starting point. If the gradient correlation (GC) is used as a comparison measure (e.g., similarity measure), the environment that maximizes the gradient correlation as:

$$\tilde{p}^g = \arg\max_{p'_j} GC(\Omega_N(\nabla I_d^{proj}, p^j), \Omega_N(\nabla I_d^{fluoro}, p'_j)), \quad (2)$$

is selected as the corresponding environment in the x-ray image, which is therefore associated with the comparison point, where:

$$GC(I_1, I_2) = \frac{1}{2}\left(NCC\left(\frac{\partial I_1}{\partial u}, \frac{\partial I_2}{\partial u}\right) + NCC\left(\frac{\partial I_1}{\partial v}, \frac{\partial I_2}{\partial v}\right)\right), \quad (3)$$

with $$NCC(I_1, I_2) = \frac{\sum((I_1(u,v) - \bar{I}_1) \cdot (I_2(u,v) - \bar{I}_2))}{\sigma_{I_1} \cdot \sigma_{I_2}}, \quad (4)$$

where s denotes the standard deviations.

Since the 3D/2D tracking has thus now been completed, the movement describing the error of the test transformation is determined from the displacement information (e.g., equivalent to the now known position of the comparison points that are to be associated with the starting points). It is beneficial in this case if a motion model describing a rigid movement of all reference structures described collectively by three-dimensional starting points associated with contour points and/or a motion model describing a rigid movement in relation in each case to individual reference structures or depth intervals and permitting a rotation and a translation are/is used as a motion model. On the assumption of rigid (e.g., inflexible) reference structures, a suitable approach is to design the motion model also in a rigid manner, at least in relation to individual reference structures or depth intervals (e.g., to aim at achieving a rigid registration). This permits further development, for example, of the approach, already pursued in DE 10 2013 214 479 A1, for determining the total movement from displacements known in the image plane, as described in DE 10 2015 208 929 A1. In this case, the use of this method, therefore, has a particularly synergistic effect in the context according to one or more of the present embodiments in that there the gradient information known based on the three-dimensional gradient dataset and the gradient comparison image plays a major role. Further, the contour point displaced due to the movement is already immediately available with the comparison point. The displaced contour point may be used immediately for the calculations, such that the displacement information is therefore implicitly included.

In reality, therefore, it may be provided in this embodiment of the method that in order to determine the motion parameters for each pair of contour point and starting point associated with the contour point in the three-dimensional dataset, which may be determined taking the depth information into account, a target plane is determined taking into account the displacement information describing the observable portion of the movement, in which target plane are located the three-dimensionally displaced starting point, the comparison point (e.g., as a two-dimensionally displaced contour point), and the position of the focus of the radiation source in the acquisition geometry (e.g., chosen as the point of origin of the coordinate system). An equation system defined by scalar products of the normal vectors of the target planes, and by a vector describing the three-dimensional starting point displaced by the movement and containing the motion parameters is formed and solved for the motion parameters. For the purpose of further explanation, the corresponding parts of DE 10 2013 214 479 A1 and DE 10 2015 208 929 A1 are, for example, considered as incorporated by reference in the present disclosure.

This embodiment is accordingly based on the finding that an equation system that, although the equation system would not be unequivocally solvable for a single contour point, becomes solvable for the majority of contour points provided may be derived according to one or more of the present embodiments. This is based on the assumption that the contour under consideration is associated with a rigid (e.g., inflexible) reference structure in the target region. The reference structure is accordingly not deformed and consequently moves in the same way at each starting point. Thus, if motion parameters that describe this movement of the rigid reference structure (or the collective movement of all rigid reference structures) are applied, the resulting equation system may be solved for the same. In the context according to one or more of the present embodiments, the acquisition geometry (e.g., projection geometry) for the x-ray images is known in this case. In practice, a fan-beam geometry is used in most cases for the acquisition of the x-ray images.

In the local neighborhood of a starting point, a small movement of the rigid reference structure leads to a change in the grayscale values at the same location only when the movement has a component in the direction of the three-dimensional gradient, described by the gradient vector $g=\nabla f(w)$, where f specifies the image function (e.g., function of the image values) of the three-dimensional image dataset and w specifies the vector associated with a starting point W. All movements extending perpendicularly to g do not change the grayscale values in the vicinity of the starting point W. However, a movement dp of the contour point P corresponding to the three-dimensional starting point W in the image plane may only be determined if the movement possesses components in the direction of the x-ray image gradient vector $\nabla I^{proj}(p)$. In this case, I denotes the function of the image values (e.g., image function) for the x-ray image. Based on this construction, it is already evident that the vectors dp and g are coplanar, since the two are linked to one another on account of the same contour. From this, there arises the underlying assumption that only movements in the directions of the three-dimensional and the two-dimensional image gradient are observable. However, since this applies to each of the pairs of starting point and contour point, and since a rigid reference structure is considered, it is nonetheless possible to derive information herefrom concerning the complete three-dimensional movement.

It transpires from the considerations just presented that the two-dimensional and three-dimensional movements are linked to one another by the target plane π, which contains the target point of the movement w+dw (e.g., the new three-dimensional position of the starting point W after the movement), the projection center C (e.g., the focus of the radiation source, which may be chosen as the origin of the coordinate system), and the moved two-dimensional contour point p+dp, (e.g., the comparison point p'). The result of these geometric considerations is that a normal vector of the target plane π that may be used as a computational means may be determined.

As also described already in DE 10 2013 214 479 A1 and DE 10 2015 208 929 A1, it may also be provided within the scope of one or more of the present embodiments that the normal vector of the respective target plane is formed as a cross product of a vector that is formed as a cross product of the gradient vector of the gradient dataset standing perpendicularly on the course of the contour in the three-dimensional image dataset at the starting point with the vector describing the three-dimensional position of the starting point in the three-dimensional image dataset, with the vector describing the three-dimensional position of the comparison point. Consequently, in formulae and in the naming conventions already introduced in the foregoing text, the normal vector n of the target plane π is yielded as $$n = \frac{(w \times g) \times p'}{\|(w \times g) \times p'\|}, \quad (5)$$

where g describes the three-dimensional gradient vector in the starting point. The target plane, which may also be referred to as the correspondence plane, is interpreted as spanned by p' and w×g. Within the scope of one or more of the present embodiments, it is however recognized that the three-dimensional gradient g is extremely sensitive to noise at w.

As a more robust variant, one embodiment provides that the normal vector of the respective target planes is formed as a cross product of a vector, which is formed as the cross product of the gradient vector of the gradient comparison image at the contour point with the vector describing the three-dimensional position of the contour point, with the vector describing the three-dimensional position of the comparison point. The cross product of w×g may thus be replaced by the cross product p×∇I$^{proj}$(p). This provides that operations are conducted entirely in the two-dimensional images. The vector (e.g., three-dimensionally defined vector) of the contour point p is nonetheless excellently determinable by the depth information. If, as mentioned, the construction is such that the projection center C is located at the origin, the following may be written for the (e.g., ultimately searched-for) moved three-dimensional contour point d+dw $$n^T(w+dw)=0, \quad (6)$$

which therefore provides that the equation system may be determined as equal to zero, starting from the setting of the scalar product of the normal vector with a vector that is formed as the sum of the vector describing the three-dimensional position of the starting point prior to the movement and the searched-for vector describing the three-dimensional displacement of the starting point due to the movement. A linear relationship is established as a result.

The motion parameters of the motion model are contained in dw. Specifically, in the case of deviation information indicating likely greater deviations, it may be beneficial in individual cases to consider the rotation completely (e.g., non-linearly) in the case of a rigid motion model. In the majority of real application cases, it is, however, possible to provide that a rotational component of the movement is assumed to be linear in order to determine a linear equation system. This therefore provides that the differential, rigid movement dw of the contour point W may be described as:

$$dw=\delta\omega \times w + dt, \quad (7)$$

where dw=θ*r is the rotation vector that describes the rotation about the angle θ by the unit vector r. dt describes the differential translation. Using equations (5), (6) and (7), a linear equation of the approximated transformation vector is yielded as $$\begin{pmatrix} n \times w \\ -n \end{pmatrix}^T \begin{pmatrix} \delta\omega \\ dt \end{pmatrix} = n^T w. \quad (8)$$

If only one contour point P with starting point W is to be considered, the equation system in formula (8) may be underdetermined. However, a plurality of contour points P with associated starting points W are considered as three-dimensional contour points. The movement of the three-dimensional contour points may be described in any case by dw and dt, with the result that conventional solution methods for linear equation systems may be used. The vector formed from dw and dt is referred to in the following as dv.

Thus, it may be provided, for example, that a RANSAC algorithm is used for solving the equation system in order to allow better detection of deviating input values or solutions ("outliers"). RANSAC algorithms are extensively known in the prior art (cf., for example, the book by R. Hartley et al. titled "Multiple View Geometry in Computer Vision (Second Edition), " Cambridge University Press (2003), pp. 153-157, pp. 161-162, or the seminal article by N. Fischler et al. titled "Random Sample Consensus: A Paradigm for Model Fitting Applications to Image Analysis and Automated Cartography, " Comm. of the ACM, 1981, Vol. 24, pp. 381-395).

In an embodiment, it is, however, provided that the equation system is solved by applying an iterative reweighted optimization algorithm that employs the least squares method by minimizing the sum of the terms of the equations, each term being provided with a weighting factor and yielding zero, for each considered pair composed of contour point and starting point. Methods of the type are known as "iteratively re-weighted least square (IRLS) optimization schemes" (cf. in this regard, for example, the article by J. A. Scales et al. titled "Robust methods in inverse theory, " in: Inverse Problems 4(4), 1988, page 1071). It has been demonstrated that the use of the IRLS scheme represents a more robust alternative to direct approaches of equally weighted solutions of the equation system. The IRLS optimization is formulated as $$\delta \hat{v} = \operatorname{argmin}_{\delta v} \sum_{i}^{N} \beta_i (a_i^T \delta v - b_i)^2, \quad (9)$$

where $$a_i = ((n_i \times w^i)^T - n_i^T)^T \in \Re^6, b_i = n_i^T w_i$$

and where $\beta_i$ denotes the weighting assigned to each equation (e.g., to each pair composed of contour point and starting point). In the IRLS optimization, the solution of the equation (9) is estimated iteratively using the Levenberg-Marquardt optimizer.

In this case, the weighting factors may beneficially be chosen as a function of the comparison measure and/or as the comparison measure for the respective comparison point. In principle, therefore, the weightings constitute an observation confidence for which the value of the comparison measure, (e.g., the gradient correlation) may be applied. In a development, the weighting factors are updated with a residual confidence during the iteration acts as a product of the original weighting factor. This provides that after the first-time initialization of the weighting factors as the comparison measure or as a function of the comparison measure, an update is performed in the k-th iteration to $\beta_i^k = \beta_{z,i} * \beta_{r,i}^k$, where the residual confidence $\beta_{r,i}^k$ is determined by the residual $$\beta_{r,i}^k \propto \frac{1}{(a_i^T \delta \hat{v} - b_i)^{(k-1)}} \quad (10)$$

of the previous iteration.

If, for example, when using the "depth layer" concept, operations are conducted with subregions of the target region that are defined by depth intervals, depth information known on account of the subregions may be used in addition to their use for determining/estimating starting points also more extensively within the scope of the method according to one or more of the present embodiments, such that it may be provided that depth information known because of the subregions is taken into account in the determination of the motion parameters and/or in the formulation of the motion model. This is beneficial, for example, when the motion model treats individual depth intervals or individual reference structures as separate, rigidly moved objects.

In addition to the method, the present embodiments also relate to a computing device that is embodied for performing the method according to one or more of the present embodiments. The computing device may be, for example, the control device of the x-ray device by which the x-ray image (or the series of x-ray images) is acquired. An x-ray device of the type may be an x-ray device having a C-arm on which the x-ray source and the x-ray detector are arranged opposite one another. These types of C-arm x-ray devices are frequently employed for the fluoroscopic monitoring of medical interventions on patients, since a vast range of projection directions are settable thanks to the maneuverability of the C-arm.

The present embodiments also relate to a computer program (e.g., stored in a non-transitory computer-readable storage medium) that performs the acts of the method when the method is executed on a computing device. The foregoing statements concerning the method and the computing device also apply to the computer program. The computer program may be stored on a non-transient data medium (e.g., on a CD-ROM).

BRIEF DESCRIPTION OF THE DRAWINGS

FIG. 1 shows a schematic diagram illustrating an exemplary overlaying of an x-ray image by data of a preoperative three-dimensional dataset using an initial transformation;

FIG. 2 shows a schematic intended to explain the workflow sequence of the method according to an embodiment;

DETAILED DESCRIPTION

Figure 3:
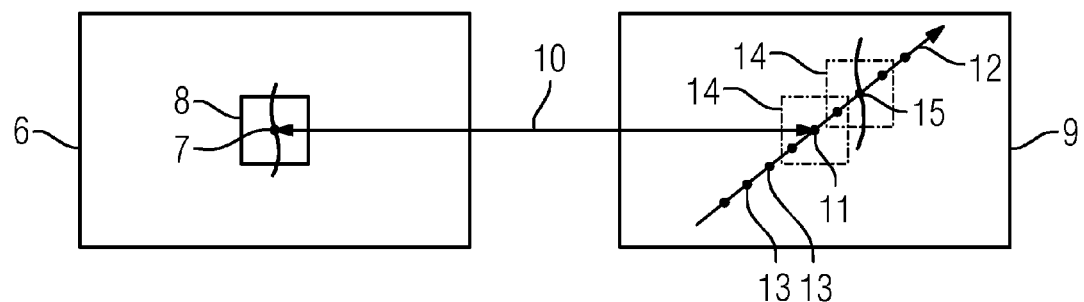
FIG. 3 shows a schematic illustrating an exemplary definition of environments and test points during 2D/3D tracking.

FIG. 1 shows, by way of example and in a schematic representation, an overlay image 1 from a three-dimensional image dataset and an x-ray image. The x-ray image 2 forms the basis onto which the information 3 of the three-dimensional image dataset is superimposed as an overlay. A shadow-like, low-resolution anatomical structure 4 (e.g., bone) is discernible in the x-ray image 2. The information 3 relating to the same anatomical structure 4, the overlaying being brought about using a coarse initial transformation (e.g., hence, a coarse 2D/3D registration), is superimposed from the three-dimensional image dataset. It is apparent that the anatomical structure according to the information 3 is slightly skewed and translated relative to the visible anatomical structure 4 of the x-ray image 2. The below-described exemplary embodiment of the method aims to determine a registration transformation that leads to an accurate overlaying of said anatomical structures, and hence, to an accurate 2D/3D registration.

In the present case, the x-ray image 2 is the first of a series of x-ray images acquired for the purpose of monitoring a medical intervention by fluoroscopic imaging. The information 3 is sourced from a preoperative three-dimensional image dataset (e.g., a CT image dataset and/or a magnetic resonance image dataset).

FIG. 2 shows a general overview of the workflow of the method according to an embodiment. In a simple overview, act S1 symbolizes the selection of contour points in a gradient comparison image that are incorporated as thinly populated (e.g., sparse) input data into the then ensuing determination of the registration transformation. From the contour points defined in act S1, starting points (e.g., "three-dimensional contour points") lying on a contour (e.g., of a reference structure) that is also visible in the x-ray image are then determined in the three-dimensional image dataset, with depth information being taken into account in the process. Act S1 may therefore be referred to overall as a "sparse input selection".

Once the contour points have been selected and corresponding starting points have been determined, a 2D/3D tracking is performed in a act S2 using gradient correlation in specific environments around contour points lying in the image plane. Two-dimensional displacements are determined by finding environments associated with a comparison point in the gradient x-ray image containing the spatial gradients of the x-ray image. The environments represent the best correspondence with the environment of the contour point in a forward-projected gradient comparison image. Act S2 may be referred to as a "2D displacement measurement".

The position of the comparison points determined in act S2 which, in conjunction with the known position of the contour points, reproduces the two-dimensional displacement information, is used in act S3 to determine, in a robust manner, the three-dimensional motion underlying the displacement of the contour points. A point-to-plane correspondence is used, and an equation system, by which the non-observable components of the three-dimensional motion may also be determined, is determined and solved. In the first pass through acts S2 and S3, motion parameters determined in this way therefore provide a correction possibility for the initial transformation adopted for use as a test transformation. The test transformation corrected with the aid of the motion parameters, which relate to a specific motion model (e.g., a rigid motion model), forms the determined registration transformation. In this case, it in an exemplary embodiment (at least in a first determination), a plurality of increasing resolutions that are used successively in order to refine the registration may be provided, thereby contributing to the robustness of the method.

However, the method is also performed iteratively in order to realize further improvements. Accordingly, in act S4, a check is carried out against an abort criterion (e.g., a maximum number of iteration processes and/or a change, even one that is extremely small) to the registration information relative to the test transformation (e.g., an abort criterion indicating a convergence). If an abort criterion or the abort criterion is satisfied, the most recently determined registration transformation is taken as the definitive registration transformation 5. This provides that the 2D/3D registration is then completed. If this is not the case, however, a 3D/2D tracking is again performed in act S2, and motion parameters are again determined in act S3 using the determined registration transformation as the new test transformation in order to find a more accurate registration transformation. In the case of the exemplary embodiment illustrated, in spite of an only very roughly estimated initial transformation, which may be derived, for example, from a known position of the patient in relation to the x-ray device recording the x-ray image, an accurate, valid 3D/2D registration may be arrived at in only 5 to 10 iteration steps.

Acts S1 to S3, and therefore the actual workflow sequence of the exemplary embodiment of the method, will now be explained in detail hereinbelow.

Once the initial transformation has been determined, in the first instance, contour points are to be determined. The contour points lie on contours that also exist in the three-dimensional image dataset. The contours, for example, may therefore correspond to contours of the anatomical structures 4 that are visible in the three-dimensional image dataset.

For this purpose, a spatial gradient dataset of the three-dimensional image dataset is first determined (e.g., a dataset in which each voxel of the three-dimensional image dataset is assigned a corresponding three-dimensional gradient vector). While a single gradient comparison image may now be determined by gradient projection according to the gradient projection theorem (cf. the article by W. Wein et al. or formula (1)), it is provided in this exemplary embodiment, in order to avoid the overlapping of structures (e.g., reference structures) of different depths along the central beam of the acquisition geometry, subregions may be defined along the central beam in order to perform a depth-aware gradient projection within the known concept of the depth intervals (cf. the article by J. Wang et al.) and consequently, a plurality of projected gradient comparison images, each corresponding to a depth interval, may be generated. The resulting stack of gradient comparison images may be denoted as $\{\nabla I_d^{proj}\}$, where d is the depth index and accordingly denotes a depth interval. The depth index is assigned as depth information to the gradient comparison image.

In the present case, the gradient comparison images are determined by using a render algorithm in a single step by a graphical processing unit (GPU). Three normalized starting channels are used for this in the present case. The first of the three normalized starting channels contains the direction of the gradient described two-dimensionally in the image plane, the second of the three normalized starting channels contains the magnitude thereof, and the third of the three normalized starting channels contains an additional, further piece of depth information (e.g., the normalized depth position within the depth interval, at which the greatest contribution to the gradient of the gradient comparison image described two-dimensionally in the image plane was present during the forward projection of the gradient image). In reality, therefore, the result of the render operation may be an output texture of the type $\text{frag}_r = \alpha_{2\pi}$
$\text{frag}_g = g_{\|-1\|}$
$\text{frag}_b = d_m,$ where the normalized angle of the gradient direction is yielded as a radian value divided by $2\pi$, the inverse normalized gradient magnitude is yielded as $$g_{\|-1\|} = \frac{1}{1 + \|g\|},$$

and $d_m$ is the depth position normalized via the maximum depth. This depth-aware gradient render operation generates the gradient position together with a depth estimation in a single render step on a GPU.

The contour points are selected in the gradient comparison image by applying a selection criterion to each image element in order to find prominent gradients that correspond to a contour. In this case, in a simple yet practical possibility, the selection criterion may include a threshold value comparison, which provides that the gradients having a magnitude that exceeds a threshold value satisfy the selection criterion. That said, however, further aspects of the selection criterion may also relate to considerations of the environment (e.g., in order to identify actually longer edges/contours that are associated with an anatomical structure 4 that lies within the subregion defined by the depth interval).

Should use be made initially of considerations at a coarser resolution in which a plurality of smaller image elements of the resolution of the x-ray image are combined into a larger image element (e.g., field or "patch"), in the present case, the definition of the gradient direction and the gradient magnitude for a "patch" of the type is used by the structure tensor for the center point (e.g., the central smaller image element) of the larger image element for the larger image element. In this case, the eigenvectors and the eigenvalues of the structure tensor are used in order to determine the gradient direction.

The object of act S2 is now to establish whether the point in the real x-ray image corresponding to the contour point actually lies at the position of the contour point or has been displaced, and if so, how strongly. For this purpose, a local gradient-based comparison may be conducted.

FIG. 3 shows by way of example, a gradient comparison image 6 with a contour point 7 through which there runs a contour (e.g., indicated). A starting point in the three-dimensional image dataset (and consequently the gradient dataset), which may also be determined by way of the depth information (e.g., the depth interval and the depth position within the interval,—may be associated with the contour point. At the starting point, it may be assumed that the three-dimensional gradient in this case stands substantially perpendicularly on the radiation direction (e.g., since the contour may be seen in the image plane).

Around the contour point 7, an environment 8, the size of which permits a useful local comparison and which is beneficially chosen as a function of a deviation transformation describing a presumed deviation of the test transformation from the valid registration transformation, is drawn. For example, there may be a variation of between 5*5 image elements and 20*20 image elements in a 512*512 image. In later iteration steps (e.g., repetitions of acts S2 and S3), it is possible in the event of convergence also to start from smaller deviations. However, a conclusion may also be drawn with respect to the initial transformation in terms of how well this applies. If, for example, it is simply a rough estimation based on the known position of the patient in the x-ray device, a greater potential deviation is likely than if, in the case of a series of x-ray images, the finally determined registration transformation 5 of the most recently acquired x-ray image is derived from an initial transformation. In a multiple resolution scheme, the current resolution level may not have an influence also on the choice of the size of the environment 8, since at a coarser resolution smaller environments may be chosen where appropriate. This is not absolutely necessary, however.

The point in the gradient x-ray image 9 corresponding in position to the contour point 7, the gradient x-ray image 9 therefore containing for each pixel of the x-ray image the spatial (e.g., two-dimensional) gradient there, will be referred to in the following as the base test point 11 (cf., arrow 10). A search direction 12 is also defined in the x-ray image 9 as the projected direction of the three-dimensional gradient in the starting point. Since depth intervals (e.g., narrow depth intervals) are used and the gradient comparison image 6 only relates to one of the depth intervals, the gradient described two-dimensionally in the image plane (e.g., the first result channel) indicates this direction sufficiently accurately and may be used directly. In a test range or search area along the search direction, test points 13 corresponding in each case to a pixel are determined as candidate positions, the number (and hence the search area) of which may also be made dependent on the already mentioned deviation information. In the present case, four further test points 13 are shown, by way of example, on either side of the base test point 11. Other numbers may be used in a real-world implementation.

An environment 14 corresponding in size to the environment 8 may also be defined for each of the test points 11, 13.

The gradient correlation (cf., the article by W. Wein et al.) as well as equation (3)) is now determined as a comparison measure between the environment 8 and each of the environments 14, of which only two are shown in FIG. 3 for reasons of clarity. The test point 11 with the maximum gradient correlation is considered to be the best correspondence (cf., equation (2)), and will be referred to hereinbelow as comparison point 15 (cf., FIG. 3). At the same time, a threshold value for the gradient correlation is used in the present case (e.g., a specific basic correlation is assumed). The comparison point 15 is discarded if the threshold value is not exceeded.

A valid comparison point 15 corresponds to the contour point 7 displaced under the influence of the movement that is to be determined and describes the error in the test transformation. The difference between the comparison point and the contour point 7 therefore indicates the two-dimensional observable displacement due to the movement.

The motion parameters thus assigned to specific displacements by 3D/2D tracking and describing the three-dimensional movement in a three-dimensional motion model, which is assumed here in simplified form as a rigid, common movement of all of the reference structures, is to be determined based on a point-to-target plane correspondence, as has been proposed by DE 10 2013 214 479 A1, such a way that the components of the three-dimensional movement that are not observable at individual points may also be reconstructed.

This will now be explained in more detail with regard to FIG. 4, which shows, by way of example, a coordinate system x, y having an origin at the focal point C of the beam source in the acquisition geometry. Also shown is a rigid reference structure 16 in the target region that is to be imaged. The reference structure 16, when radiographed, has a contour that extends in the present case perpendicularly to the viewing plane of FIG. 4 in the resulting x-ray image. A contour point 7, or P, that is also contained accordingly in the three-dimensional image dataset as starting point W is part of this contour. The contour point W in the three-dimensional image dataset therefore lies on a contour and, if recourse is made to the acquisition geometry and the test transformation, is projected onto the contour point P in the two-dimensional projection image (e.g., x-ray image, in the image plane 17, in the case of a correct test transformation, as shown by the beam trajectory 18). As shown, the three-dimensional gradient vector g stands perpendicularly on the radiation direction.

In order to simplify the illustration, the image plane 17 is shown by way of example as lying at "1" in the corresponding coordinate. An x-ray detector or an actual position is not necessarily required to define this because a rescaling is possible without difficulty. The calculations then become significantly easier, as also by virtue of the position of the focal point C, since the latter, as already explained hereinabove, is also part of the target plane π.

In the actual x-ray image, the comparison point 15 or P' corresponds to the starting point W, which provides that the movement describing the error in the test transformation has displaced the contour point P by the just determined displacement dp relative to the comparison point or the displaced contour point P'.

The corresponding three-dimensional movement has displaced the starting point W in accordance with the vector dw to the displaced starting point W'. If a rigid movement with differential rotation is assumed, dw is yielded according to formula (7). The vectors contained therein are likewise shown in FIG. 4. The vectors dw, dw×w and dt do not necessarily have to lie within the viewing plane of FIG. 4, which is described by C, W and the gradient vector g. Within a local neighborhood of the starting point W, a small movement of the reference structure 16 leads merely to a change in the grayscale values at the same location if the movement has a component in the direction of the gradient vector g, which, as has already been explained in the general description, is contained in the three-dimensional gradient dataset. All movements extending orthogonally to g produce no change in the grayscale values in the vicinity of the point W. Accordingly, a movement dp of the point P in the x-ray image may be identified only when the movement dp of the point P extends in the direction of the x-ray image gradient vector $\nabla I_d^{proj}(p)$ Since the vectors dp and g are both derived from the same contour, the vectors dp and g are coplanar. As a result, only movements in the direction of the two-dimensional and three-dimensional gradients of the image data are at all observable.

Figure 4:
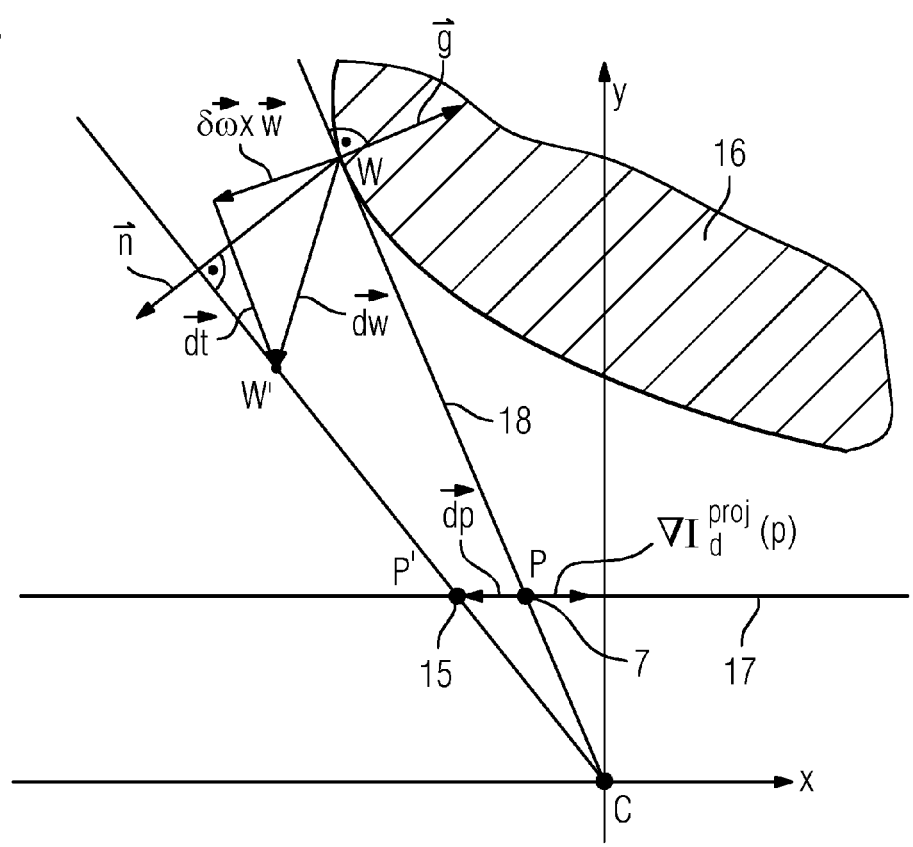
FIG. 4 shows a schematic illustrating an exemplary definition of the correspondence plane in preparation for the setting up of the equation system.

The two-dimensional and three-dimensional movements are linked to one another by the target plane $\pi$, which is likewise shown in FIG. 4 and, in addition to the target point of the movement describing the error of the test transformation, contains w+dw, the focal point C as the position of the radiation source, and the moved contour point P' in the x-ray image, p+dp (e.g., a comparison point).

The normal vector n of the target plane $\pi$ is also depicted accordingly in FIG. 4 and may be determined by formula (5), although the present exemplary embodiment provides, as a more robust variant (and one managing without explicit use of the starting point), that the cross product $p \times \nabla I_d^{proj}(p)$ is used instead of the cross product w×g as a robust alternative, which is likewise possible (cf., FIG. 4).

As described, the displacements determined during the 3D/2D tracking and the error in the test transformation described by the motion parameters are related by formula (6), which produces the equation system. The motion parameters (e.g., the rotation dw and the translation dt) are still to be determined by the point-to-plane correspondence model given by equation (6) (cf., in this regard, also formulas (7) and (8)), which may be solved using conventional methods (e.g., a RANSAC method) for the equation system that is linear by virtue of the assumption of the differential rotation.

In the present case, it is, however, provided that use be made of the IRLS optimization scheme, as has been described with regard to equation (9). The weightings $\beta_i$ are given as described via the gradient correlation and in the different iteration steps by the residual confidence.

Figure 5:
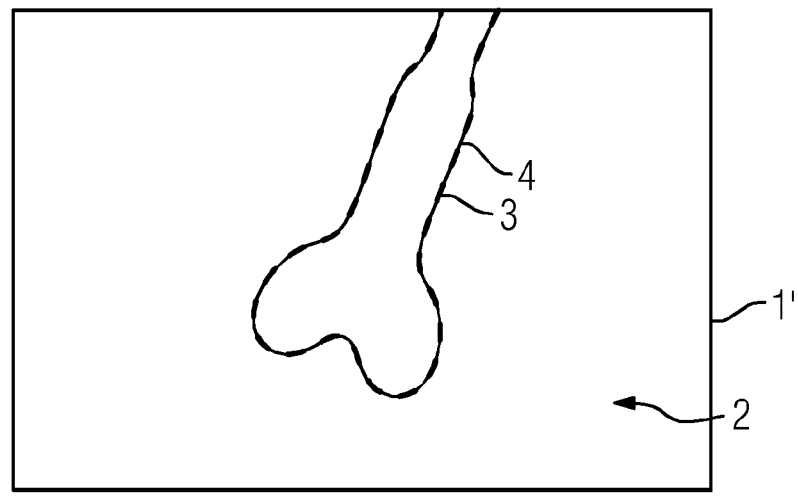
FIG. 5 shows the overlaying of FIG. 1 with the ultimately determined registration transformation.

Once the motion parameters have first been ascertained, the registration transformation may be determined in act S3, as the test transformation corrected by the transformation described by the motion parameters. The process is then continued further in an iterative manner, as has been described already with regard to FIG. 2. The result of the 2D/3D registration according to an embodiment is shown in FIG. 5, where the finally resulting registration transformation 5 is applied for accurately superposing the information 3 on the anatomical feature 4 in the overlay image 1'.

Figure 6:
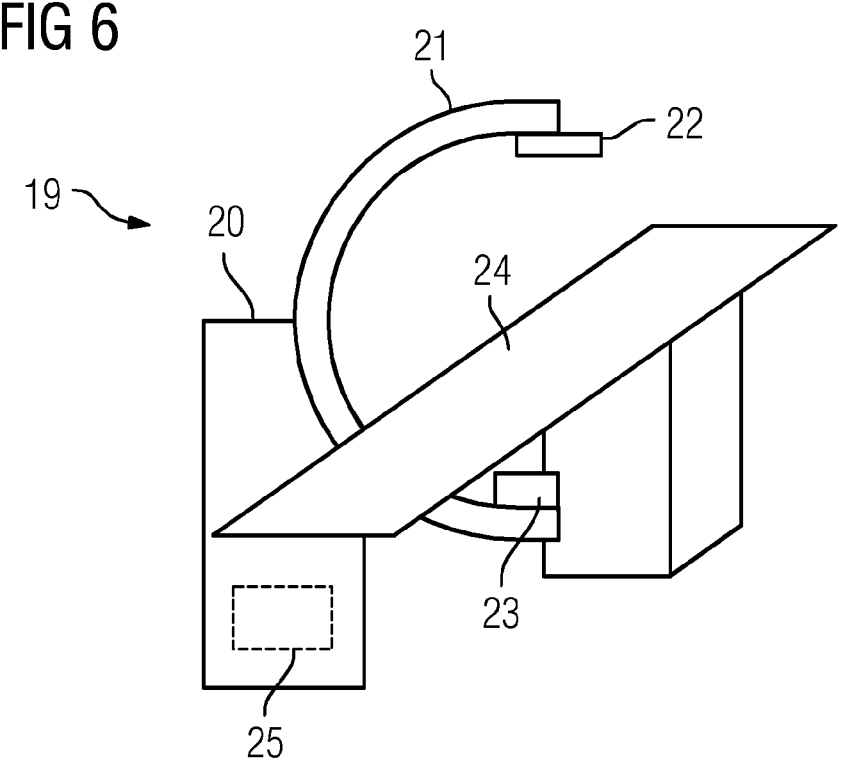
FIG. 6 shows one embodiment of an x-ray device.

FIG. 6 shows a schematic diagram of an x-ray device 19 by which the illustrated exemplary embodiment of the method may be performed. The x-ray device 19 has a C-arm 21 that is mounted on a retaining stand 20 and on which an x-ray detector 22 and an x-ray source 23 (or radiation source 23) are arranged opposite one another. The C-arm 21 may be moved (e.g., swiveled) relative to a patient support platform 24 in order to enable different acquisition geometries and projection angles to be set that are suitable during the medical treatment (e.g., minimally invasive treatment) of a patient.

The x-ray device 19 also has a control device 25 (e.g., a controller including a processor) that is embodied as a computing device for performing the method.

Although the invention has been illustrated and described in more detail on the basis of the exemplary embodiments, the invention is not limited by the disclosed examples, and other variations may be derived herefrom by the person skilled in the art without leaving the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for registering a three-dimensional (3D) image dataset of a target region of a patient with a two-dimensional (2D) x-ray image of the target region recorded in an acquisition geometry, the method comprising:
    following specification of an initial transformation as a test transformation that is to be optimized:
        determining a 2D gradient x-ray image and a 3D gradient dataset of the image dataset;
        determining at least one 2D gradient comparison image forward-projected in the acquisition geometry of the x-ray image using the test transformation from the 3D gradient dataset after the determining of the 2D gradient x-ray image and the 3D gradient dataset of the image dataset, wherein depth information describing a depth in a radiation direction of a central beam of the acquisition geometry is associated in the at least one 2D gradient comparison image with gradients described two-dimensionally in an image plane;
        carrying out a check for each image element of the at least one 2D gradient comparison image to determine whether the gradient described two-dimensionally in the image plane satisfies a selection criterion indicating the presence of a contour in the image element, wherein all image elements satisfying the selection criterion are selected as contour points;
        determining an environment that best corresponds to a local environment of the contour point based on a comparison measure, and extends around a comparison point in the gradient x-ray image for all contour points in the at least one gradient comparison image from a plurality of environments extending around test points;
        determining local 2D displacement information, the determining of the local 2D displacement information comprising comparing the contour points with the associated comparison points; and
        determining motion parameters of a 3D motion model that describe a movement of the target region between the acquisition of the image dataset and the x-ray image from the local 2D displacement information and a registration transformation describing the registration by correcting the test transformation based on the motion parameters.

2. The method of claim 1, further comprising determining a plurality of gradient comparison images for different depth intervals of the 3D image dataset in the radiation direction of the central beam of the acquisition geometry,
  wherein the respective depth interval is assigned to the at least one 2D gradient comparison image as depth information, for each of the at least one 2D gradient comparison image, the depth position in relation to the radiation direction in the depth interval covered by the at least one 2D gradient comparison image, at which position a maximum contribution to the gradient occurred during the forward projection, is assigned as depth information to each gradient described two-dimensionally in the image plane, or a combination thereof.

3. The method of claim 2, wherein the at least one 2D gradient comparison image is determined by applying a render algorithm to the gradient dataset, and
  wherein one result channel of the render algorithm contains a normalized angular value as a direction indication of the gradient in the image plane, and a further result channel contains a measure for a magnitude of the gradient in the image plane.

4. The method of claim 3, wherein during determination of the depth position as depth information, a third result channel that contains the depth position normalized by the extension of the covered depth interval is used.

5. The method of claim 3, wherein the render algorithm is executed by a GPU.

6. The method of claim 1, wherein the selection criterion comprises a threshold value comparison for the magnitude of the gradient described two-dimensionally in the image plane.

7. The method of claim 1, wherein the 2D gradient x-ray image and the at least one 2D gradient comparison image are initially determined in a coarser resolution with larger image elements than the x-ray image, and
  wherein the determination of the motion parameters and the correction of the test transformation are repeated successively to at least provide a better resolution.

8. The method of claim 7, wherein the determination of the motion parameters and the correction of the test transformation are repeated successively to at least provide a resolution up to a resolution of the 2D x-ray image.

9. The method of claim 7, wherein the gradients of a larger image element formed by a plurality of image elements of a size of the image elements of the 2D x-ray image are determined at least for the 2D gradient x-ray image from a structure tensor of the larger image element.

10. The method of claim 1, wherein the method is repeated iteratively with the registration transformation as a new test transformation until an abort criterion is satisfied.

11. The method of claim 10, wherein the abort criterion is an undershooting of a threshold value for a norm of the motion parameters, the exceeding of a predetermined number of iteration steps, or a combination thereof.

12. The method of claim 1, wherein a coarse transformation determined from a known position of the patient relative to the x-ray device acquiring the x-ray image, a coarse transformation determined from a registration process using forward-projected virtual x-ray images and performed at a coarser resolution, a coarse transformation having an accuracy of less than 20 mm with respect to translations, less than 10° with respect to rotations, or a combination thereof is used as a first used initial transformation.

13. The method of claim 1, further comprising acquiring a time series of x-ray images,
  wherein a registration is performed for each x-ray image of the time series of x-ray images, and the registration transformation determined for the previously acquired x-ray image is used in each case as the initial transformation.

14. The method of claim 11, wherein in the case of a registration transformation determined for an x-ray image acquired immediately beforehand, a smaller environment, a smaller number of test points, or a combination thereof is chosen as the initial transformation than in the case of any other initial transformation.

15. The method of claim 1, wherein in addition to a base test point corresponding to the contour point, test points are chosen along the direction of the gradient projected onto the image plane in the starting point associated with the contour point.

16. The method of claim 1, further comprising:
  determining comparison measures for a specific number of test points corresponding to one image element in each case; and
  choosing the test point associated with the comparison measure indicating a greatest correspondence as the comparison point or choosing the test points by an optimization algorithm maximizing the comparison measure and operating along the direction of the projected three-dimensional gradient in the starting point associated with the contour point.

17. The method of claim 1, wherein the test points, the number of test points, or the test points and the number of test points to be used are determined as a function of deviation information describing a degree of a present deviation of the test transformation from reality.

18. The method of claim 17, wherein motion parameters of at least one registration process in relation to an x-ray image acquired at an earlier point in time, prediction information derived therefrom, or a combination thereof is used as deviation information.

19. The method of claim 1, wherein the associated 2D displacement information is discarded if a minimum value for the comparison measure at the comparison point is undershot.

20. The method of claim 1, wherein the gradient correlation is used as the comparison measure.

21. The method of claim 1, wherein a motion model permitting a rotation and a translation and describing a rigid movement of all reference structures described by 3D starting points associated with contour points, in relation to individual reference structures, depth intervals, or a combination thereof is used as the motion model.

22. The method of claim 1, wherein in order to determine the motion parameters for each pair of contour point and starting point associated with the contour point in the 3D image dataset, which is determinable taking into account the depth information, taking into account the displacement information describing the observable component of the movement, a target plane, in which the three-dimensionally displaced starting point, the comparison point, and the focal point of the radiation source in the acquisition geometry, is determined, the focal point being chosen as a point of origin of the coordinate system, are located, whereupon an equation system formed by setting the scalar products of the respective normal vector of the target planes and a vector describing the starting point displaced three-dimensionally due to the movement and containing the motion parameters to zero is formed and solved for the motion parameters.

23. The method of claim 22, wherein the normal vector of the respective target planes is formed as a cross product of a vector that is formed as the cross product of the gradient vector of the gradient dataset standing perpendicularly on the course of the contour in the 3D image dataset at the starting point with the vector describing the 3D position of the starting point in the 3D image dataset or of the gradient vector of the at least one 2D gradient comparison image at the contour point with the vector describing the 3D position of the contour point, with the vector describing the 3D position of the comparison point.

24. The method of claim 22, wherein a rotational component of the movement is assumed as linear in order to determine a linear equation system.

25. The method of claim 22, wherein the equation system is solved by applying an iterative, reweighted optimization algorithm that employs the least squares method, by minimizing the sum of the terms of the equations for the contour points, each term being provided with a weighting factor and yielding zero.

26. The method of claim 25, wherein the weighting factors are determined as a function of the comparison measure, as the comparison measure for the respective comparison point, or a combination thereof.

27. The method of claim 26, wherein the weighting factors are updated during the iteration steps as a product of the original weighting factor with a residual confidence.

28. The method of claim 1, wherein depth information known based on subregions is taken into account in the determination of the motion parameters, in the formulation of the motion model, or in the determination of the motion parameters and in the formulation of the motion model.

29. A controller of an x-ray device for registering a three-dimensional (3D) image dataset of a target region of a patient with a two-dimensional (2D) x-ray image of the target region recorded in an acquisition geometry, the controller comprising:
   a processor configured to:
      following specification of an initial transformation as a test transformation that is to be optimized:
         determine a 2D gradient x-ray image and a 3D gradient dataset of the image dataset;
         determine at least one 2D gradient comparison image forward-projected in the acquisition geometry of the x-ray image using the test transformation from the 3D gradient dataset after the determining of the 2D gradient x-ray image and the 3D gradient dataset of the image dataset, wherein depth information describing a depth in a radiation direction of a central beam of the acquisition geometry is associated in the at least one 2D gradient comparison image with gradients described two-dimensionally in an image plane;
      carry out a check for each image element of the at least one 2D gradient comparison image to determine whether the gradient described two-dimensionally in the image plane satisfies a selection criterion indicating the presence of a contour in the image element, wherein all image elements satisfying the selection criterion are selected as contour points;
      determine an environment that best corresponds to a local environment of the contour point based on a comparison measure, and extends around a comparison point in the gradient x-ray image for all contour points in the at least one gradient comparison image from a plurality of environments extending around test points;
      determine local 2D displacement information, the determining of the local 2D displacement information comprising comparing the contour points with the associated comparison points; and
      determine motion parameters of a 3D motion model that describe a movement of the target region between the acquisition of the image dataset and the x-ray image from the local two-dimensional displacement information and a registration transformation describing the registration by correcting the test transformation based on the motion parameters.

30. In a non-transitory computer-readable storage medium storing instructions executable by a computing device to register a three-dimensional (3D) image dataset of a target region of a patient with a two-dimensional (2D) x-ray image of the target region recorded in an acquisition geometry, the instructions comprising:
   following specification of an initial transformation as a test transformation that is to be optimized:
      determining a 2D gradient x-ray image and a 3D gradient dataset of the image dataset;
      determining at least one 2D gradient comparison image forward-projected in the acquisition geometry of the x-ray image using the test transformation from the 3D gradient dataset after the determining of the 2D gradient x-ray image and the 3D gradient dataset of the image dataset, wherein depth information describing a depth in a radiation direction of a central beam of the acquisition geometry is associated in the at least one 2D gradient comparison image with gradients described two-dimensionally in an image plane;
   carrying out a check for each image element of the at least one 2D gradient comparison image to determine whether the gradient described two-dimensionally in the image plane satisfies a selection criterion indicating the presence of a contour in the image element, wherein all image elements satisfying the selection criterion are selected as contour points;
   determining an environment that best corresponds to a local environment of the contour point based on a comparison measure, and extends around a comparison point in the gradient x-ray image for all contour points in the at least one gradient comparison image from a plurality of environments extending around test points;
   determining local 2D displacement information, the determining of the local 2D displacement information comprising comparing the contour points with the associated comparison points; and
   determining motion parameters of a 3D motion model that describe a movement of the target region between the acquisition of the image dataset and the x-ray image from the local two-dimensional displacement information and a registration transformation describing the registration by correcting the test transformation based on the motion parameters.

* * * * *